(12) United States Patent
Ogura

(10) Patent No.: US 6,197,796 B1
(45) Date of Patent: Mar. 6, 2001

(54) ANTICANCER COMPOSITION COMPRISING A DIAMINOTRIFLUOROMETHYLPYRIDINE DERIVATIVE

(75) Inventor: Yoshifumi Ogura, Tsu (JP)

(73) Assignee: Ishihara Sangyo Kaisha Ltd., Osaka (JP)

(*) Notice: Subject to any disclaimer, the term of this patent is extended or adjusted under 35 U.S.C. 154(b) by 0 days.

(21) Appl. No.: 09/355,957

(22) PCT Filed: Feb. 26, 1998

(86) PCT No.: PCT/JP98/00776

§ 371 Date: Aug. 17, 1999

§ 102(e) Date: Aug. 17, 1999

(87) PCT Pub. No.: WO98/37887

PCT Pub. Date: Sep. 3, 1998

(30) Foreign Application Priority Data

Feb. 28, 1997 (JP) .................................... 9-60083

(51) Int. Cl.$^7$ .................................................. A61K 31/44
(52) U.S. Cl. ............................................. 514/352; 514/336
(58) Field of Search ...................................... 514/352, 336

(56) References Cited

U.S. PATENT DOCUMENTS 5,492,908 * 2/1996 Haga et al. ........................ 514/228.8

OTHER PUBLICATIONS

Steiner et al., Drug News & Perspectives, vol. 7(6), pp. 344–351, 1994.*

* cited by examiner

*Primary Examiner*—Jerome D. Goldberg
(74) *Attorney, Agent, or Firm*—Oblon, Spivak, McClelland, Maier, & Neustadt, P.C.

(57) ABSTRACT

An anticancer composition comprising a diaminotrifluoromethylpyridine derivative of the formula (I) or its pharmaceutically acceptable salt, as an active ingredient:

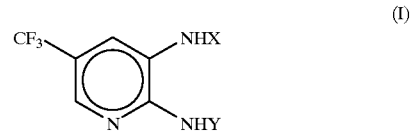

wherein X is a cycloalkylcarbonyl group, a furancarbonyl group or a benzoyl group which may be substituted by a halogen atom, and Y is an alkylsulfonyl group.

8 Claims, No Drawings

ANTICANCER COMPOSITION COMPRISING A DIAMINOTRIFLUOROMETHYLPYRIDINE DERIVATIVE

TECHNICAL FIELD

The present invention relates to an anticancer composition comprising a diaminotrifluoromethylpyridine derivative or its pharmaceutically acceptable salt, as an active ingredient.

BACKGROUND ART

EP0465913-A discloses that a diaminotrifluoromethylpyridine derivative or its salt has a phospholipase $A_2$ inhibition activity and thus is useful as an active ingredient of an anti-inflammatory agent or an anti-pancreatitis agent. Further, the same publication discloses that in platelets or cells related to inflammatory symptoms, phospholipase $A_2$ is secreted or activated by various stimulations and contributes to the production of a platelet activating factor (PAF) or some arachidonic acid methabolites, and that the arachidonic acid methabolites have been found to be closely related to various diseases, for example, inflammatory symptoms such as rheumatoid arthritis, arthritis deformans, tenontitis, psoriasis and related dermatitis; nasal and bronchial airway troubles such as allergic rhinitis and allergic bronchial asthma; and immediate hypersensitive reactions such as allergic conjunctivitis. On the other hand, it is disclosed that phospholipase $A_2$ secreted from pancreas is activated in the intestine and exhibits a digestive action, but once activated in the pancreas, it is believed to be one of the factors causing pancreatitis. And, it is disclosed that the above diaminotrifluoromethylpyridine derivative or its salt inhibits phospholipase $A_2$ and thus is effective for the treatment of the above-mentioned diseases caused by phospholipase $A_2$ such as inflammatory symptoms, nasal and bronchial airway troubles, immediate hypersensitive reactions or pancreatitis. Thus, it is disclosed to be useful as an anti-inflammatory agent, an agent for treating bronchial asthma, an anti-allergy agent, an anti-pancreatitis agent, anti-nephritis agent, or anti-MOF (Multiple Organ Failure).

DISCLOSURE OF THE INVENTION

It is an object of the present invention to provide an anticancer composition comprising a diaminotrifluoromethylpyridine derivative or its pharmaceutically acceptable salt, as an active ingredient.

The present inventors have conducted various studies on the pharmacological activities of the diaminotrifluoromethylpyridine derivative or its salt. As a result, they have found that such a compound has a suppressive effect of carcinogenesis useful as an anticancer agent. The present invention has been accomplished on the basis of this discovery.

That is, the present invention provides an anticancer composition comprising a diaminotrifluoromethylpyridine derivative of the formula (I) or its pharmaceutically acceptable salt, as an active ingredient:

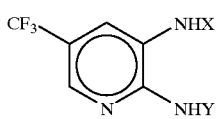

(I)

wherein X is a cycloalkylcarbonyl group, a furancarbonyl group or a benzoyl group which may be substituted by a halogen atom, and Y is an alkylsulfonyl group.

Now, the present invention will be described in detail with reference to the preferred embodiments.

The cycloalkylcarbonyl group for X in the diaminotrifluoromethylpyridine derivative of the formula (I) may be one wherein the cycloalkyl moiety has from 5 to 8 carbon atoms, such as cyclopentylcarbonyl, cyclohexylcarbonyl, cycloheptylcarbonyl or cyclooctylcarbonyl. The halogen atom as the substituent on the benzoyl group for X, may be fluorine, chlorine, bromine or iodine. The alkylsulfonyl group for Y may be one wherein the alkyl moiety has from 1 to 18 carbon atoms, such as methylsulfonyl, ethylsulfonyl, propylsulfonyl, butylsulfonyl, pentylsulfonyl, hexylsulfonyl, heptylsulfonyl, octylsulfonyl, decylsulfonyl or nonadecylsulfonyl, and such an alkyl moiety may be of a straight chain structure or a branched chain structure.

The salt of the diaminotrifluoromethylpyridine derivative may be any salt so long as it is a pharmaceutically acceptable salt. For example, an alkali metal salt such as a potassium salt or a sodium salt, an alkaline earth metal salt such as a calcium salt, or an organic amine salt such as a triethanolamine salt or a tris(hydroxymethyl)aminomethane salt may be mentioned. Among such salts, some may have crystal water.

Specific examples of the diaminotrifluoromethylpyridine derivative of the formula (I) or its salt, include N-(2-ethylsulfonylamino-5-trifluoromethyl-3-pyridyl) cyclohexane-carboxamide or its sodium salt, N-(2-isopropylsulfonylamino-5-trifluoromethyl-3-pyridyl) cyclopentane-carboxamide, N-(2-methylsulfonylamino-5-trifluoromethyl-3-pyridyl)-2-furancarboxamide, N-(2-methylsulfonylamino-5-trifluromethyl-3-pyridyl)-4-fluorobenzamide, and N-(2-isopropylsulfonylamino-5-trifluoromethyl-3-pyridyl)-3-fluorobenzamide.

The diaminotrifluoromethylpyridine derivative or its pharmaceutically acceptable salt is useful as an active ingredient of an anticancer composition. Particularly, such a compound has a suppressive effect of carcinogenesis and is effective, for example, for suppressing multiple carcinogenesis after removal of solid tumor. Such multiple carcinogenesis may take place in a case of e.g. superficial bladder cancer, hepatic cancer or lung cancer, and the compound suppresses relapse of such a cancer after removal of the solid tumor. The relapse process after removal of the solid cancer includes a phenomenon such as invasion or implantation of cancer cells released by the removal to the surrounding tissues (so-called tumor metastasis). Such a compound has been found to have an inhibitory activity against cell adhesion and cell infiltration, as one of its activities. Thus, such a compound is expected to be effective also for suppressing tumor metastasis. Further, such a compound suppresses a progress from colic polypus to colon cancer, or a progress from hyperplasia by papilloma virus to uterine cervix cancer.

To administer the diaminotrifluoromethylpyridine derivative or its salt as an active ingredient of an anticancer composition, it is formulated alone or together with a pharmaceutically acceptable carrier into a drug composition suitable for peroral, or parenteral administration, such as a tablet, a powder, a capsule, a granule, an injection drug, an ointment, an inhalant or a suppository, and it is administered in the form of such a drug formulation.

As a drug formulation suitable for peroral administration, a solid composition such as a tablet, a capsule, a powder, a granule or a troach; or a liquid composition such as a syrup suspension, may be mentioned. The solid composition such as a tablet, a capsule, a powder, a granule or a troach may contain a binder such as fine crystalline cellulose, gum arabic, tragacanth gum, gelatin or polyvinyl pyrrolidone; an excipient such as starch, lactose or carboxymethyl cellulose; a disintegrator such as alginic acid, corn starch or carboxymethyl cellulose; a lubricant such as magnesium stearate, light silicic anhydride or colloidal silicon dioxide; a sweetener such as sucrose; or a flavoring agent such as peppermint or methyl salicylate. The liquid composition such as a syrup or a suspension may contain sorbitol, gelatin, methyl cellulose, carboxymethyl cellulose, a vegetable oil such as a peanut oil, an emulsifier such as lecithin as well as a sweetener, a preservative, a colorant or a flavoring agent, as the case requires. Such a composition may be provided in the form of a dried formulation. These formulations may contain from 1 to 95% by weight of the active compound.

A drug formulation suitable for parenteral administration may, for example, be an injection drug, an inhalant, an ointment or a suppository. The injection drug may be prepared by dissolving the compound in the form of a salt in usual water for injection, or may be formulated into a formulation suitable for injection such as a suspension or an emulsion (in a mixture with a pharmaceutically acceptable oil or liquid). In such a case, it may contain benzyl alcohol as an antibacterial agent, ascorbic acid as an antioxidant, a pharmaceutically acceptable buffer solution or a reagent for adjusting the osmotic pressure. Such an injection drug preferably contains from 0.1 to 50% by weight of the active compound.

The inhalant may be formulated by dissolving the compound of the present invention alone or together with a pharmaceutically acceptable inert carrier in an aerosol or nebulizer solution, or may be administered to the resiratory airway in the form of fine powder for inhalation. In the case of fine powder for inhalation, the particle size is usually not more than 50 μm, preferably not more than 10 μm. Such an inhalant may be used, if necessary, in combination with other antiasthematic agent or bronchodilator.

An ointment may be prepared by a conventional method by an addition of a commonly employed base or the like. The ointment may contain from 0.1 to 30% by weight of the active compound.

The suppository may contain a carrier for formulation, such as polyethylene glycol, lanolin, cacao butter or fatty acid triglyceride. The suppository may contain from 1 to 95% by weight of the active compound.

The above-mentioned drug compositions suitable for peroral or parenteral administration, may be formulated by conventional methods so that after administration to a patient, the active component will be rapidly discharged, gradually discharged or belatedly discharged.

The dose of the active ingredient varies depending upon the type of the compound, the administration method, the condition of the patient or the animal to be treated. The optimum dose and the number of administration under a specific condition must be determined by the judgment of a competent doctor. Usually, however, a daily dose to an adult is from about 0.1 mg to about 10 g, preferably from about 1 mg to about 1 g. In the case of the above inhalation method, the dose of the compound of the present invention is preferably from about 0.01 mg to about 1 g per administration.

Now, specific Formulation Examples of the anticancer composition of the present invention will be given.

| FORMULATION EXAMPLE 1 (tablet) | |
|---|---|
| (1) Active ingredient | 20 mg |
| (2) Lactose | 150 mg |
| (3) Starch | 30 mg |
| (4) Magnesium stearate | 6 mg |

The above composition is tabletted so that the components (1) to (4) constitute one tablet.

| FORMULATION EXAMPLE 2 (powder, microgranule or granule) | |
|---|---|
| (1) Active ingredient | 20 mg |
| (2) Sugar ester | 180 mg |
| (3) Surfactant | 15 mg |
| (4) Light silicic anhydride | 25 mg |

The components (1) to (4) are mixed to obtain a powder drug. Then, the mixture is granulated to obtain a microgranule or granule.

Such a powder, microgranule or granule may be sealed in a capsule to obtain a capsule drug.

| FORMULATION EXAMPLE 3 (hard gelatin capsule) | |
|---|---|
| (1) Active ingredient | 25 mg |
| (2) Starch | 200 mg |
| (3) Magnesium stearate | 10 mg |

The components (1) to (3) are packed in a hard gelatin-capsule to obtain a hard gelatine capsule drug.

| FORMULATION EXAMPLE 4 (injection drug) | |
|---|---|
| (1) Active ingredient | 1 mg |
| (2) D-mannitol | 10 mg |
| (3) Tris(hydroxymethyl)aminomethane | 2.16 mg |

A tris buffer containing the components (1) to (3) is freeze-dried to obtain an injection drug.

| FORMULATION EXAMPLE 5 (ointment for external skin application) | |
|---|---|
| (1) Active ingredient | 0.5 g |
| (2) White vaseline | 25 g |
| (3) Stearyl alcohol | 22 g |
| (4) Propylene glycol | 12 g |
| (5) Sodium lauryl sulfate | 1.5 g |
| (6) Ethyl para-hydroxybenzoate | 0.025 g |
| (7) Propyl para-hydroxybenzoate | 0.015 g |
| (8) Purified water | 100 g |

The components (1) to (8) are formulated into an ointment for external skin application by a usual method for preparation of an ointment.

BEST MODE FOR CARRYING OUT THE INVENTION

TEST EXAMPLE 1

Suppressive Effect of Carcinogenesis Against BOP-Induced Biliary Tract Cancer of Hamster The common duct for the bile duct and the pancreatic duct of a female Syrian golden hamster of five weeks old was subjected to ligature ablation, followed by cholecystduodenostmy, to obtain an experimental model in which pancreatic fluid flowed backward into the biliary tract. From one week after the operation, N-nitrosobis(2-oxopropyl)amine (carcinogen BOP) was subcutaneously administered in an amount of 10 mg/kg once every week for ten weeks, and the hamster was fed the normal diet for 16 weeks (control group).

To a test group, 200 ppm of sodium salt of N-(2-ethylsulfonylamino-5-trifluoromethyl-3-pyridyl) cyclohexane carboxamide was administered as mixed with the normal diet for 16 weeks.

After termination of feeding period, histopathological examination of the gallbladder and the bile duct was carried out. The results are shown in Table 1.

TABLE 1

|  | Control group | Test group |
| --- | --- | --- |
| n | 19 | 9 |
| Gallbladder cancer | 15 (78.9%) | 3 (33.3%) |
| Bile duct cancer | 7 (36.8%) | 0 (0%) |

In the control group (n=19), biliary tract cancer resulted in a high ratio i.e. gallbladder cancer: 78.9% and bile duct cancer: 36.8%. Whereas, in the test group (n=9), formation of biliary tract cancer was suppressed as compared with the control group to a level of gallbladder cancer: 33.3% and bile duct cancer: 0%.

From the histopathological type, in the control group, tubular adenocarcinoma constituted 25.6%, while in the test group, each was papillary adenocarcinoma, and transfer to anaplastic type was found to be suppressed as compared with the control group.

What is claimed is:

1. A method of postoperatively suppressing carcinogenesis sensitive to the compounds of formula I, comprising:
    administering a carcinogenesis suppressing effective amount of a diaminotrifluoromethylpyridine derivative of formula (I) or its phamaceutically acceptable salt thereof:

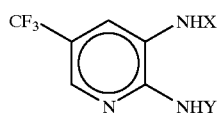

(I)

wherein X is cycloalkylcarbonyl, furancarbonyl or benzoyl, each of which optionally is substituted by a halogen atom, and Y is alkylsulfonyl, in a pharmaceutically acceptable excipient, to a human patient or an animal.

2. The method according to claim 1, wherein the diaminotrifluoromethylpyridine compound is administered at a dosage of 0.1 mg to 1 g/day to said human patient or animal.

3. The method according to claim 2, wherein said dosage is 1 mg to 1 g/day.

4. The method according to claim 1, wherein said administration is effective in suppressing superficial bladder cancer, hepatic cancer or lung cancer.

5. A method of inhibiting tumor cell adhesion and tumor cell infiltration sensitive to the compounds of formula I, comprising:
    administering an inhibiting effective amount of a diaminotrifluoromethylpyridine derivative of formula (I) or its phamaceutically acceptable salt thereof:

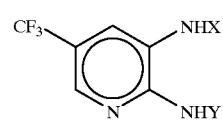

(I)

wherein X is cycloalkylcarbonyl, furancarbonyl or benzoyl, each of which optionally is substituted by a halogen atom, and Y is alkylsulfonyl, in a pharmaceutically acceptable excipient, to a human patient or an animal.

6. The method according to claim 5, wherein the administration of said compound is effective in suppressing tumor metastasis.

7. A method of suppressing the progress of colic polypus to colon cancer, comprising:
    administering a suppressing effective amount of a diaminotrifluoromethylpyridine derivative of formula (I) or its phamaceutically acceptable salt thereof:

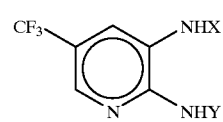

(I)

wherein X is cycloalkylcarbonyl, furancarbonyl or benzoyl, each of which optionally is substituted by a halogen atom, and Y is alkylsulfonyl, in a pharmaceutically acceptable excipient, to a human patient or an animal.

8. A method of suppressing the progress of hyperplasia by papilloma virus to uterine cervical cancer, comprising:
    administering an inhibiting effective amount of a diaminotrifluoromethylpyridine derivative of formula (I) or its phamaceutically acceptable salt thereof:

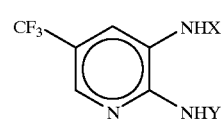

(I)

wherein X is cycloalkylcarbonyl, furancarbonyl or benzoyl, each of which optionally is substituted by a halogen atom, and Y is alkylsulfonyl, in a pharmaceutically acceptable excipient, to a human patient or an animal.

* * * * *